United States Patent [19]

Matsuda

[11] Patent Number: 5,538,494
[45] Date of Patent: Jul. 23, 1996

[54] RADIOACTIVE BEAM IRRADIATION METHOD AND APPARATUS TAKING MOVEMENT OF THE IRRADIATION AREA INTO CONSIDERATION

[75] Inventor: Koji Matsuda, Hitachi, Japan

[73] Assignee: Hitachi, Ltd., Tokyo, Japan

[21] Appl. No.: 405,858

[22] Filed: Mar. 17, 1995

[30] Foreign Application Priority Data

Mar. 17, 1994 [JP] Japan .................................. 6-046795

[51] Int. Cl.⁶ .................................................. A61N 5/10
[52] U.S. Cl. .............................. 600/1; 600/2; 250/492.3; 378/65
[58] Field of Search .................. 250/492.3; 378/65; 128/395 R, 396, 714, 721; 600/1, 2

[56] References Cited

U.S. PATENT DOCUMENTS 5,039,867  8/1991  Nishihara et al. ................... 250/492.3
5,427,101  6/1995  Sachs et al. ........................... 128/721

FOREIGN PATENT DOCUMENTS 6-154348  6/1994  Japan .................................. 600/1

Primary Examiner—Jack I. Berman
Attorney, Agent, or Firm—Antonelli, Terry, Stout & Kraus

[57] ABSTRACT

A radiation irradiation method and an apparatus enables effective radiation irradiation even in the case of a diseased part changing its position due to physical activity, such as breathing and the heart beat of the patient, with a simplified apparatus. Initially, the position change of the diseased part and the physical activity of the patient are measured concurrently, and a relationship therebetween is defined as a corresponding function. Next, along with the detection of the physical activity of the patient, radiation therapy is performed, in which the control of the radiation irradiation is carried out in accordance with the corresponding function.

9 Claims, 15 Drawing Sheets

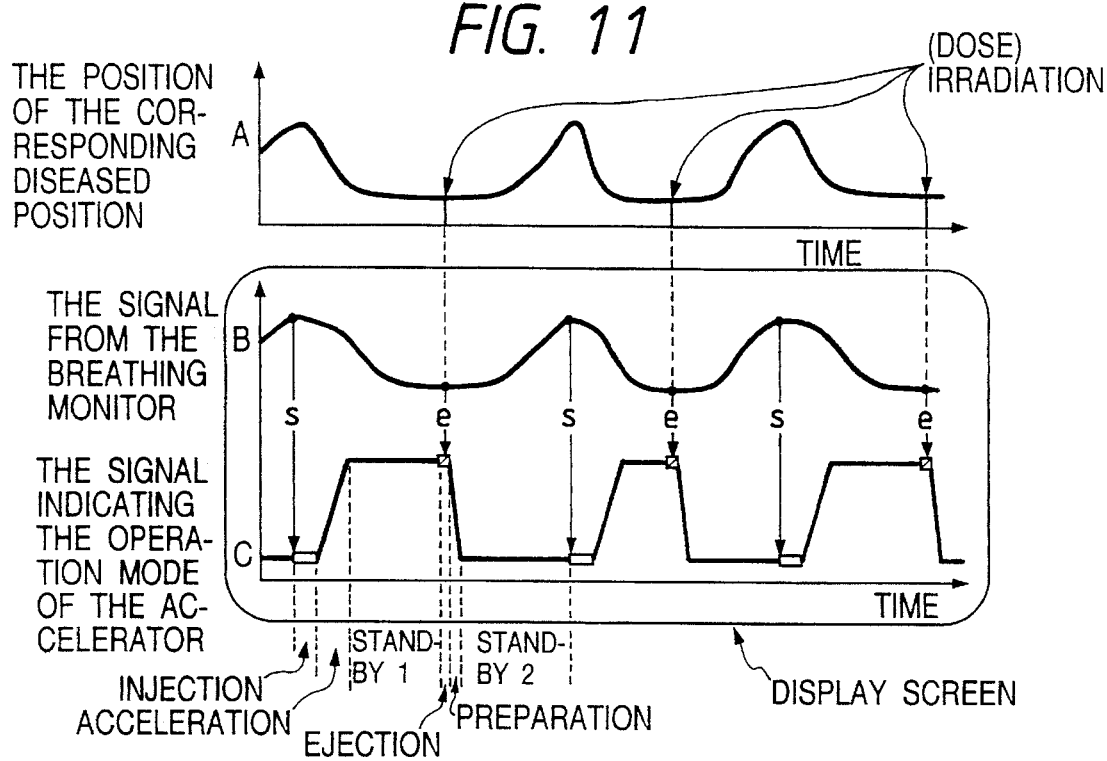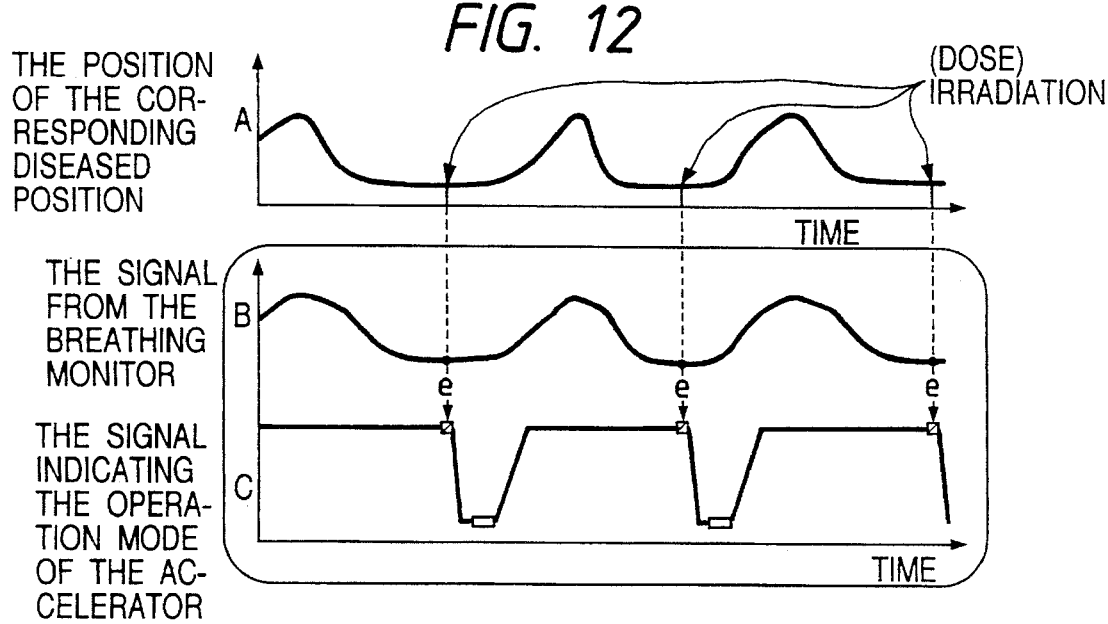

s : STARTING OF THE OPERATION SEQUENCE
e : STARTING THE EJECTION
o : TERMINATING THE EJECTION
▨ : IN THE EJECTION
▢ : INJECTION
→ : THE TRIGGER SIGNAL TO THE CYNCROTRON CONTROL PART s : STARTING OF THE
    OPERATION SEQUENCE
e : STARTING THE EJECTION
o : TERMINATING THE
    EJECTION

▨ : IN THE EJECTION
▢ : INJECTION
⟶ : THE TRIGGER SIGNAL
    TO THE CYNCROTRON
    CONTROL PART s : STARTING OF THE OPERATION SEQUENCE
e : STARTING THE EJECTION
o : TERMINATING THE EJECTION

▨ : IN THE EJECTION
▢ : INJECTION
→ : THE TRIGGER SIGNAL TO THE CYNCROTRON CONTROL PART

RADIOACTIVE BEAM IRRADIATION METHOD AND APPARATUS TAKING MOVEMENT OF THE IRRADIATION AREA INTO CONSIDERATION

BACKGROUND OF THE INVENTION

The present invention relates to a radiation irradiation method and a radioactive beam irradiation apparatus.

In Japanese Patent Application Laid-Open No. 59-88160 (1984), there is disclosed a radiation irradiation control apparatus for controlling a target area of beam irradiation by detecting a three-dimensional position of a diseased part using an ultrasonic tomography apparatus.

In general, in radiation therapy using proton and heavy particles, the resolution of the target position of the irradiation is higher, and thus, there is an advantage that a proper dose of irradiation to the diseased part can be obtained. However, in case the position of the diseased part is subject to physical activity, such as movement due to breathing and heart beat, the dose to be irradiated to the diseased position is reduced and hence, the expected effect for the therapy can not be attained. The physical movement and similar phenomena, such as movement caused by breathing and heart beat, is designated "physical activity". In the prior art, since real-time control of the irradiation direction and position is necessary, with the diseased position measurement being carried out in real-time as well, a complex apparatus is necessary for measuring the position of the diseased part and for controlling the radiation therapy apparatus.

SUMMARY OF THE INVENTION

An object of the present invention is to provide a radiation irradiation method and a radiation irradiation apparatus enabling radiation irradiation to a diseased part moving in response to physical activity with a simple apparatus configuration.

The first aspect of the invention for attaining the above object is to obtain the relation between a detected signal and a position change of the diseased part beforehand by detecting the time change of the physical activity of the patient beforehand, and during the radiation irradiation, to detect the time change of the physical activity of the patient and to synchronize the radiation irradiation timing with the detected signal.

The second aspect of the invention uses a radiation irradiation apparatus which has a detector for measuring a time change of physical activity of the patient;

an information processing apparatus, connected to a memory apparatus for storing a relation between the detected signal indicating the time change of physical activity of the patient and the position change of the diseased position, and for determining the radiation irradiation timing based on the detected signal from the detector and the information from the memory means; and a radiation control means for controlling the timing in response to the output signal from the information processing apparatus.

The position change of the diseased part during the radiation therapy is subject to the physical activity of the patient. Therefore, to measure the change in the physical activity of the patient in a time domain is interpreted as an indirect measurement of the position change of the diseased part. By detecting the physical activity of the patient corresponding to the position change of the diseased part, and synchronizing the radiation irradiation timing to the physical activity, the control of the radiation irradiation in response to the position change of the diseased part can be established resultantly.

In the first aspect of the invention, by preparing the relation between the detected signal and the position change of the diseased part beforehand, the measurement of the position change of the diseased part can be replaced for the measurement of the time change of the physical activity which can be configured with a simple apparatus. With this approach, the direct measurement of the position change of the diseased part, which inevitably requires a complex apparatus and a control mechanism operating in real-time during the radiation irradiation, can be eliminated, and the radiation irradiation can be applied even to a diseased part whose position is subject to physical activity, with a simple apparatus configuration.

In the second aspect of the invention, by storing the relation between the detected signal and the position change of the diseased part in the memory means, the position change of the diseased part can be obtained from a real-time detected signal using an information processing apparatus connected to the memory apparatus. With this approach, the direct measurement of the position change of the diseased part, which inevitably requires a complex apparatus and control mechanism operating in real-time during the radiation irradiation, can be eliminated, and an apparatus with a simple configuration can be realized so that the radiation irradiation may be applied even to a diseased part whose position is subject to physical activity.

BRIEF DESCRIPTION OF THE DRAWINGS

FIG. 11 is a timing chart showing the time change of the position of a diseased part (A), the output signal from a breathing monitor (B), and the operation state (C) of a synchrotron using a fast ejection method, in which a single irradiation action is activated by two trigger signals during a single breathing action of the patient.

FIG. 12 is a timing chart showing the time change of the position of a diseased part (A), the output signal from a breathing monitor (B), and the operation state (C) of a synchrotron using a fast ejection method, in which a single irradiation action is activated by a single trigger signal during a single breathing action of the patient.

DETAILED DESCRIPTION OF THE PREFERRED EMBODIMENTS

Figure 1:
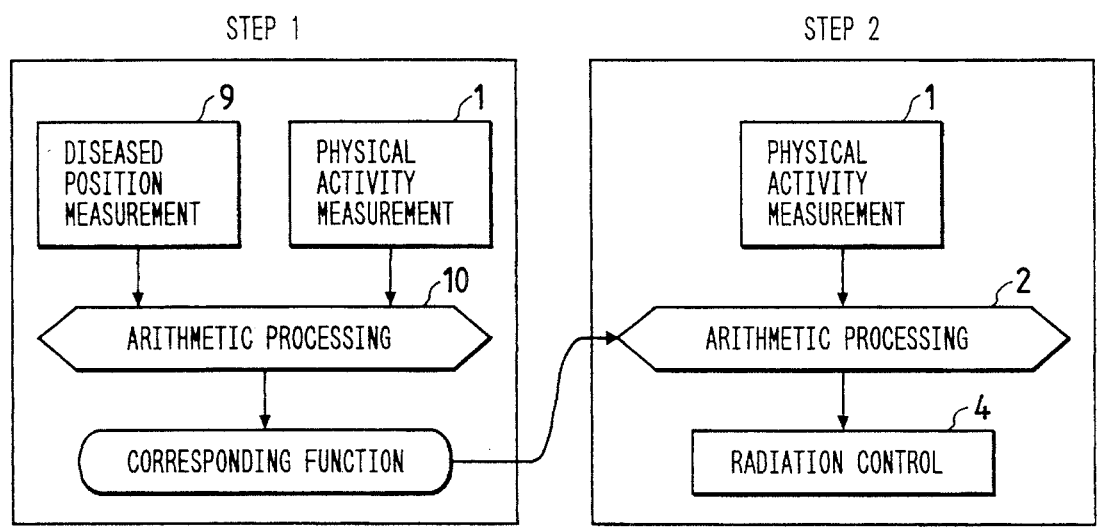
FIG. 1 is a flowchart showing procedures for radiation therapy according to the present invention.

The method of radiation therapy according to the present invention uses two steps, as shown in FIG. 1. In the step 1 in FIG. 1, by measuring the position change of the diseased part and the time change of the physical activity of the patient, the relation between those changes (designated "corresponding function") is defined explicitly. Next, in the step 2 in FIG. 2, the radiation therapy goes on along with the real-time measurement of the time change of the physical activity of the patient. The control of the radiation irradiation is based on the corresponding function defined in the step 1. In the following, by referring to FIGS. 2 to 8, an embodiment of the apparatus of the present invention and its control mechanism will be described A method and apparatus for radiation therapy using charged particle beams, when the movement of the diseased part is synchronized to the heart beat of the patient, will be described.

Figure 2:
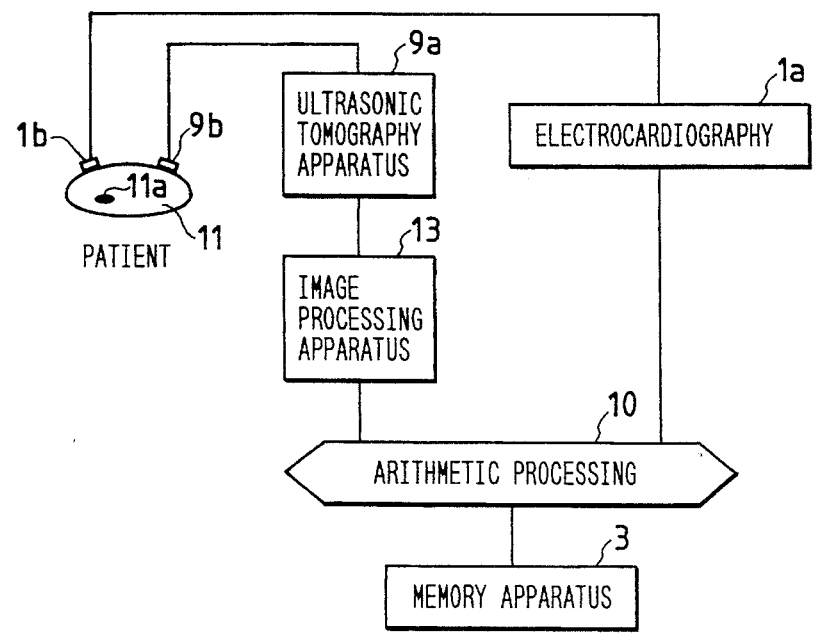
FIG. 2 is a block diagram of an apparatus for measuring the electrocardiogram of a patient and the movement of a diseased position of the patient.
Figure 4:
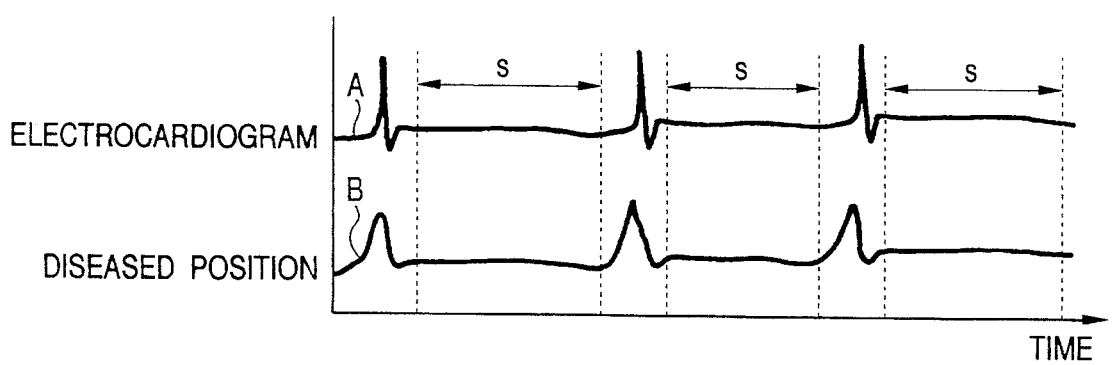
FIG. 4 is a timing chart of the electrocardiogram of a patient and the movement of a diseased position of the patient.

In FIG. 2, the component 9a is a ultrasonic tomography apparatus, which obtains a tomographic image of an area neighboring a diseased part of a patient from the ultrasonic signal detected by a probe 9b. By image processing, the position of the diseased part is identified. The component 1a is a electrocardiograph, which generates a electrocardiogram from a signal received from the electrode 1b. FIG. 4 is an example of the measured data of the electrocardiogram and the position of the diseased part. The curve A is a part of the electrocardiogram and the curve B is the position of the diseased part. The change in the position of the diseased part is in synchronism with the curve A of the electrocardiogram, and during the period s, the position of the diseased part does not significantly change. The discrimination condition with which the period s is identified on the detected signal on the electrocardiogram is determined by the arithmetic processing apparatus 10 in FIG. 2, and this condition is stored in the memory apparatus 3. This discrimination condition is the corresponding function shown in FIG. 1, and the procedures up to here correspond to the step 1 in FIG. 1. Though the position of the diseased part is defined in one-dimensional representation for explanation, the above procedures can be applied to the case of three-dimensional position measurement. In addition, the procedures for defining the discrimination condition for identifying the period s in which the position of the diseased position does not change, does not need to coincide with the measurement of the tomographic image, but the image processing and data analysis can be done after measurement.

Figure 3:
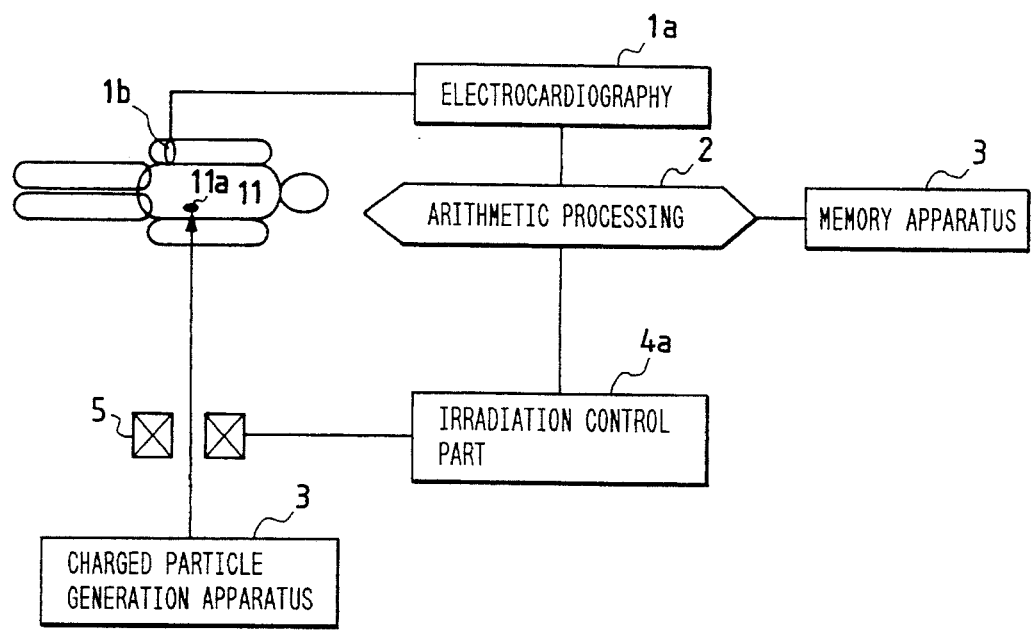
FIG. 3 is a block diagram of a radiation therapy apparatus using charged particles to be ejected in synchronization with the heart beat of a patient.

Next, the procedure in the step 2 in FIG. 1 will be described. In FIG. 3, the irradiated area by the charged particle beam generation apparatus 12 is set to be the position of the diseased part and the irradiation is carried out during the period s shown in FIG. 4. The components 1a and 1b are the electrocardiograph and its electrode used in the step 1. The signal from the electrocardiograph 1a is supplied to the arithmetic processing apparatus 2. The arithmetic processing apparatus 2 judges the period s based on the discrimination condition stored in the memory apparatus 3, and supplies its output signal to the irradiation control part 4a. The irradiation control part 4a controls the kicker magnet 5, and controls the charged particle beam to effect irradiation during the period s.

A method and apparatus for synchronizing the operation of the accelerator for generating charged particle beams to the breathing of the patient, when the movement of the diseased part is synchronized to the heart beat of the patient, will be described.

Figure 5:
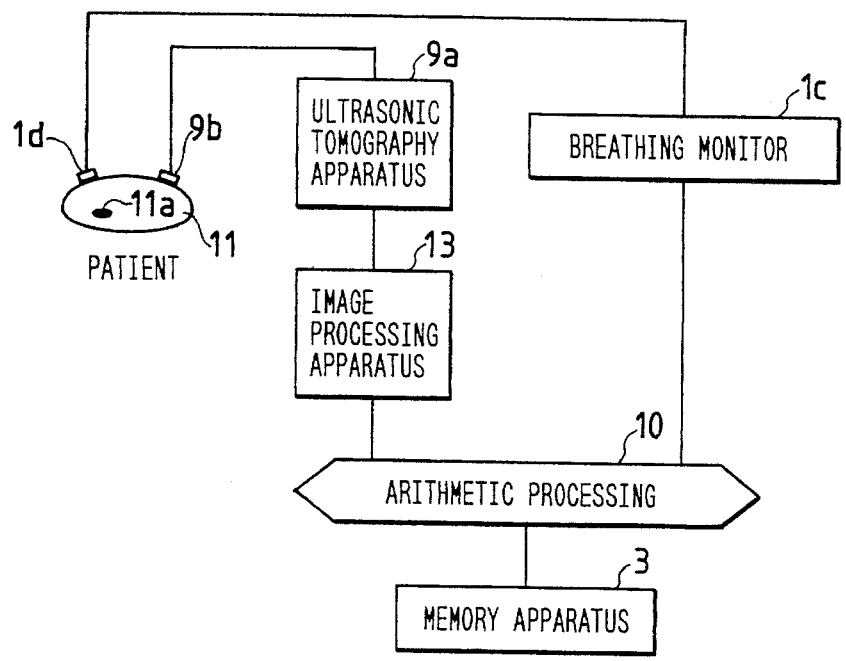
FIG. 5 is a block diagram of the apparatus for synchronizing the breathing timing of a patient and the movement of a diseased position of the patient.

In FIG. 5, the position of the diseased part is measured in a similar manner to the embodiment 1. The curves A and B are examples of the measured data from the breathing monitor and the position of the diseased part. The curve A represents an output signal from the breathing monitor, and the curve B represents the position of the position of the diseased part. The position change of the diseased part is synchronized with to the output signal A from the breathing monitor, and it is observed that the position of the diseased part does not significantly change in the period s in FIG. 7. The discrimination condition with which the period s is identified on the detected signal from the breathing monitor is determined by the arithmetic processing apparatus 10, and this condition is stored in the memory apparatus 3. This discrimination condition is the corresponding function shown in FIG. 1, and the procedures up to here correspond to the step 1 in FIG. 1.

Figure 6:
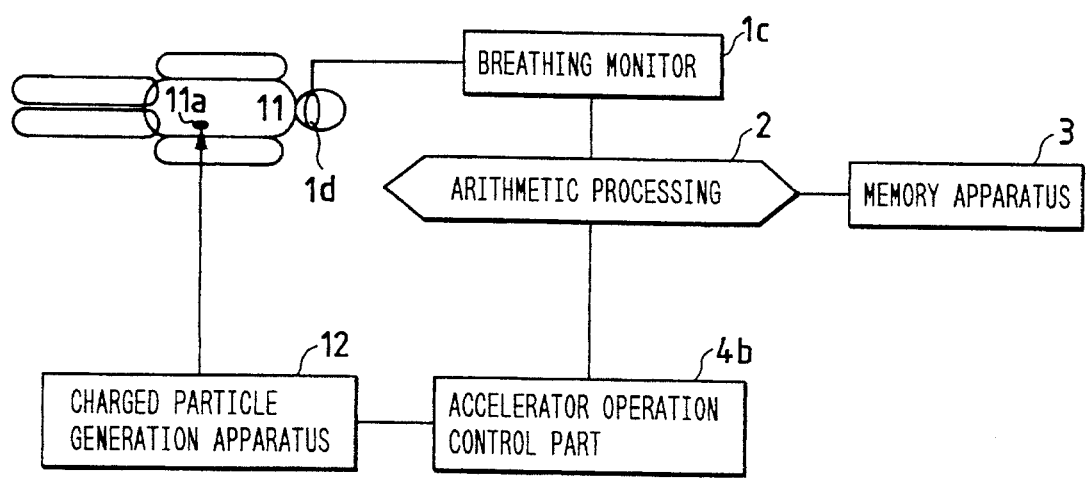
FIG. 6 is a block diagram of a radiation therapy apparatus using charged particles for controlling an accelerator operation mode in synchronization with the breathing timing of a patient.

Next, the procedure corresponding to the step 2 in FIG. 1 is described. In FIG. 6, the area irradiated by the charged particle beam generation apparatus 12 is set to be the position of the diseased part and the irradiation is carried out during the period s shown in FIG. 7. The components 1c and 1d are the identical breathing monitor and its sensor used in the step 1. The signal from the breathing monitor 1c is supplied to the arithmetic processing apparatus 2. The arithmetic processing apparatus 2 judges the period s based on the discrimination condition stored in the memory apparatus 3, and supplies its output signal to the accelerator operation control part 4b, which controls the timings of injection i and ejection e of the charged particles at the accelerator, as shown in the curve in FIG. 7. The curve C represents the trajectory of operation modes of the accelerator categorized into preparation r, injection i, acceleration a, waiting w and ejection e.

Especially, if the movement of the diseased part in response to the breathing is known to be generally and commonly applied to every patient, and if the time, when the position change of the diseased part becomes small in response to the signal from the breathing monitor, is explicitly known, it is not necessary to measure the correspondence between the physical activity and the position of the diseased part for every patient.

Figure 7:
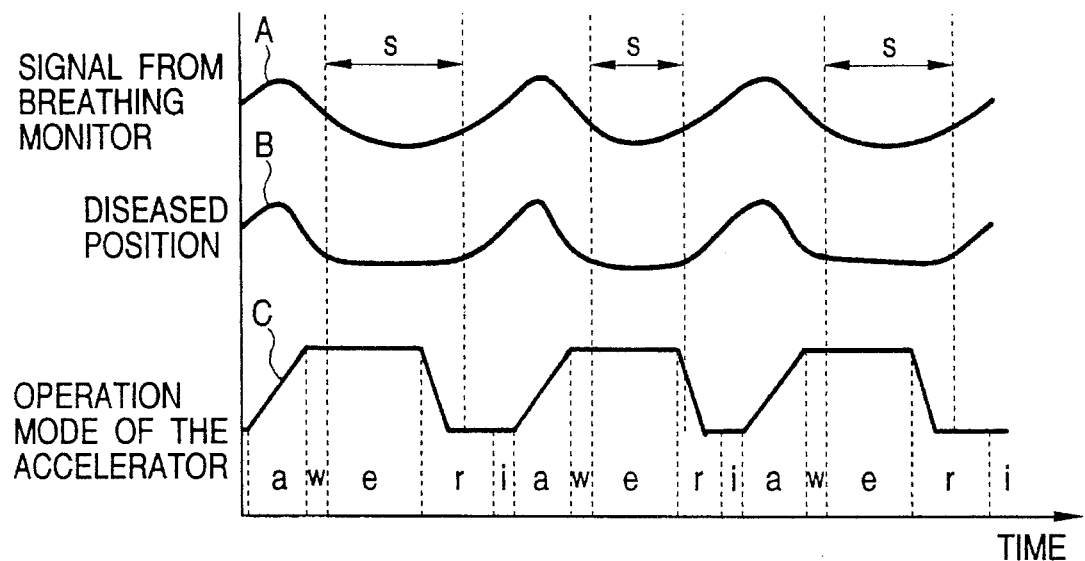
FIG. 7 is a timing chart showing an example of the changes in the breathing of a patient and in the diseased position of the patient in the time domain and the operation mode of the accelerator.

A method and apparatus for radiation therapy for adjusting the irradiation area of the charged particle beam onto the diseased part with modification of the step 2 in the embodiment of FIGS. 5–7 will be described.

In step 1, the apparatus configuration as shown in FIG. 5 is used. The signal from the breathing monitor 1c and the position change of the diseased part are measured. The position change of the diseased part is synchronized with the signal from the breathing monitor, where a definite synchronization pattern exists. A typical pattern is sampled and captured by digital processing by the arithmetic processing apparatus 10 and is stored in the memory apparatus 3.

Figure 8:
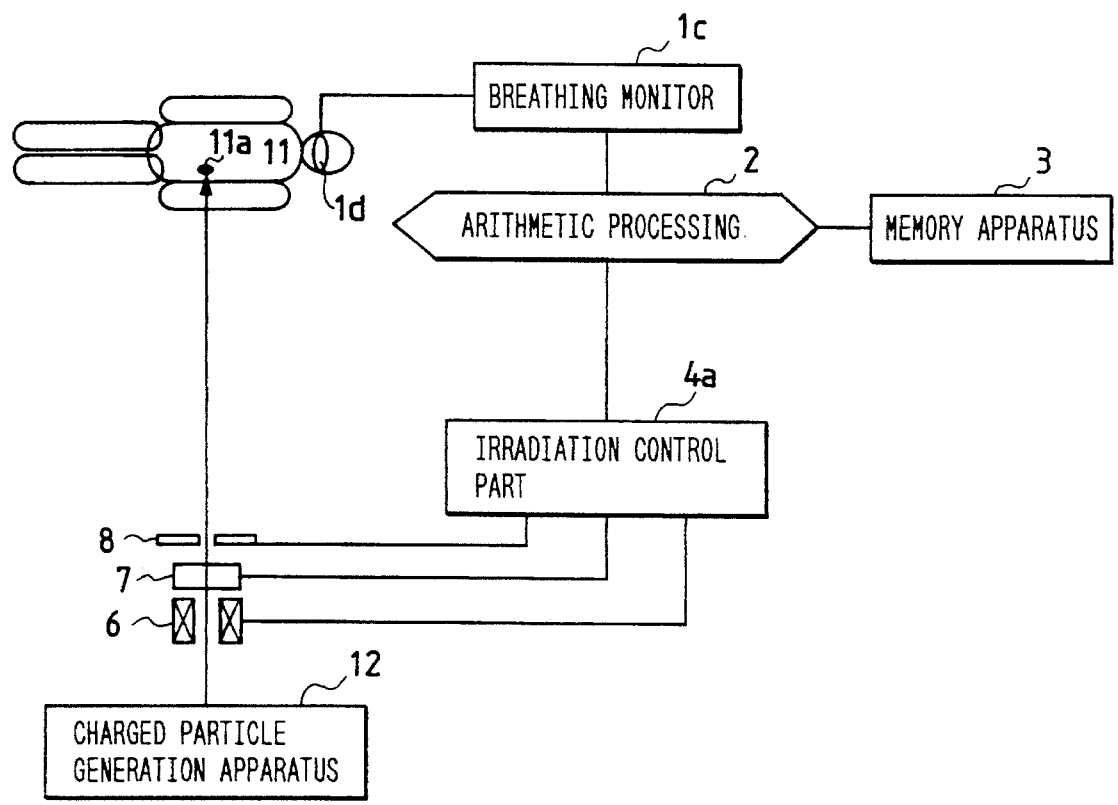
FIG. 8 is a block diagram of a radiation therapy apparatus using charged particles for adjusting the irradiation region of the radioactive ray to the movement of a diseased position in response to the breathing timing of a patient.

Next, the procedure corresponding to the step 2 in FIG. 1 will be described. In FIG. 8, the output signal from the breathing monitor 1c is supplied to the arithmetic processing apparatus 2. The arithmetic processing apparatus 2 is connected to the memory apparatus 3 and generates the pattern stored in step 1 in synchronism with the output signal from the breathing monitor. This pattern represents the approximate position of the diseased part. The information of the position of the diseased part is supplied to the irradiation control part 4a. The irradiation control part 4a controls the deflector 6 and the range shifter 7 so that the charged particle beam may be directed to the position of the diseased part designated by the input information. When the shape of the diseased part changes in addition to its position, the shape of the charged particle beam is adjusted by controlling the multiple-sectored collimator 8. In addition, in case of determining the irradiation area by extending the scanning of the charged particle beam for the diseased part over a wider area, the area of scanning is adjusted by synchronizing the patterns of the shape and position change of the diseased part to the signal from the breathing monitor.

Radiation therapy by a method similar to the one mentioned above can be applied not only to a radiation therapy apparatus using charged particle beams, but also to a radiation therapy apparatus using x-ray, r-ray and neutron beams and laser light.

In the method for controlling irradiation timing described above, since the radiation is applied to the diseased part only when the diseased part has moved to the definite position, the irradiation position defined before the irradiation operation is valid during the irradiation operation, even for a diseased part moving due to physical activity, and hence, a complex real-time control is not necessary. Therefore, even for a diseased part moving due to physical activity, the radiation irradiation can be done with a simple apparatus configuration. In addition, the efficiency of the radiation irradiation can be raised by defining the irradiation timing when the position change of the diseased part is small.

In case movement of a diseased part commonly applicable to all patients is known generally, it is not necessary to obtain the correspondence between the physical activity and the position of the diseased part for each individual patient, which leads to further simplification of the apparatus and control mechanism.

In the method for obtaining the approximate position of a diseased part by measuring the physical activity as in the embodiment of FIG. 6, the irradiation direction and area can be adapted to the diseased part. Since the position of the diseased part is measured beforehand, it is not necessary to measure a complex change in the position of the diseased part in real-time, and hence, a fast image processing and its control mechanism can be simplified.

Next, there will be described an apparatus synchronizing its operation to the breathing of the patient, and in its own operation, in the radiation operation performed thereby, when the position change of the diseased part is in synchronism with the breathing of the patient, after the charged particle beam is accelerated by a synchrotron, a short plus beam is ejected with an ejection method designated "fast ejection method" and is irradiated onto the diseased part.

Figure 9:
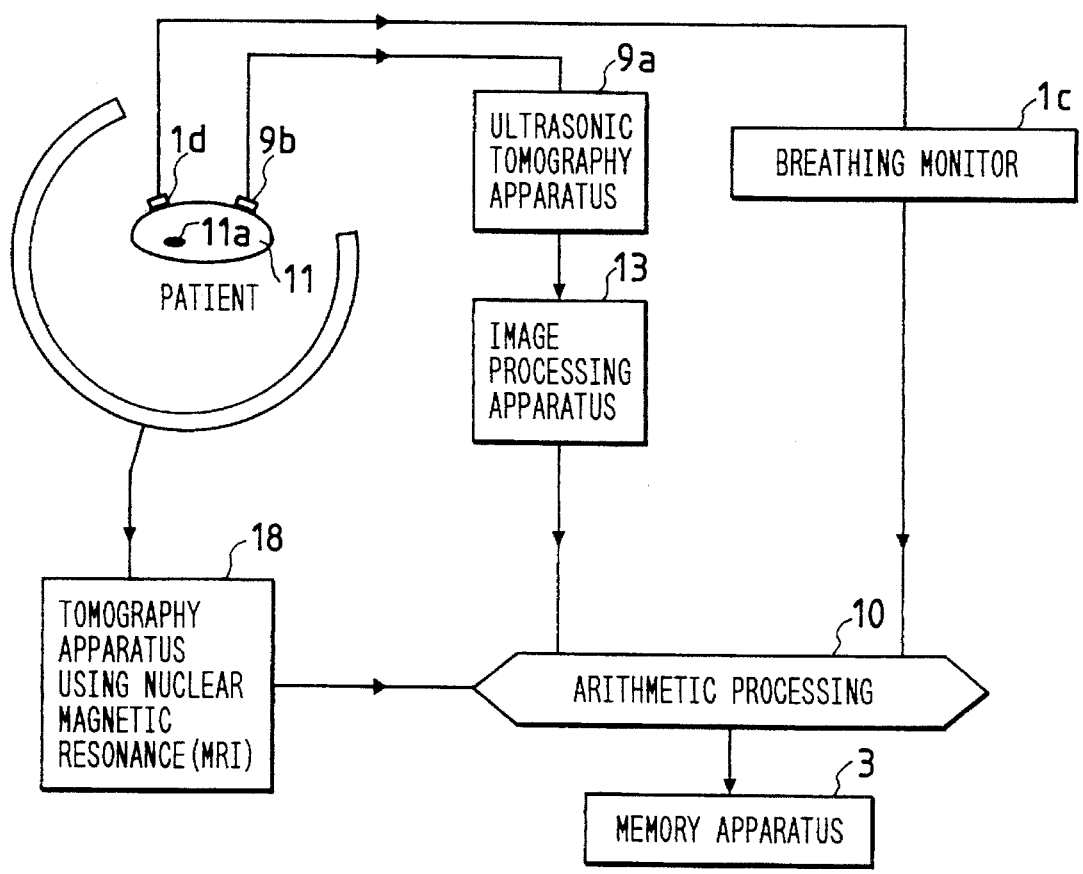
FIG. 9 is a diagrammatic configuration of an apparatus for producing a correlation between the breathing of a patient and the position change of a diseased part of the patient, in which the position of the diseased part is measured by a combination of an ultrasonic tomography apparatus and a tomography apparatus using a nuclear magnetic resonance method (MRS).
Figure 10:
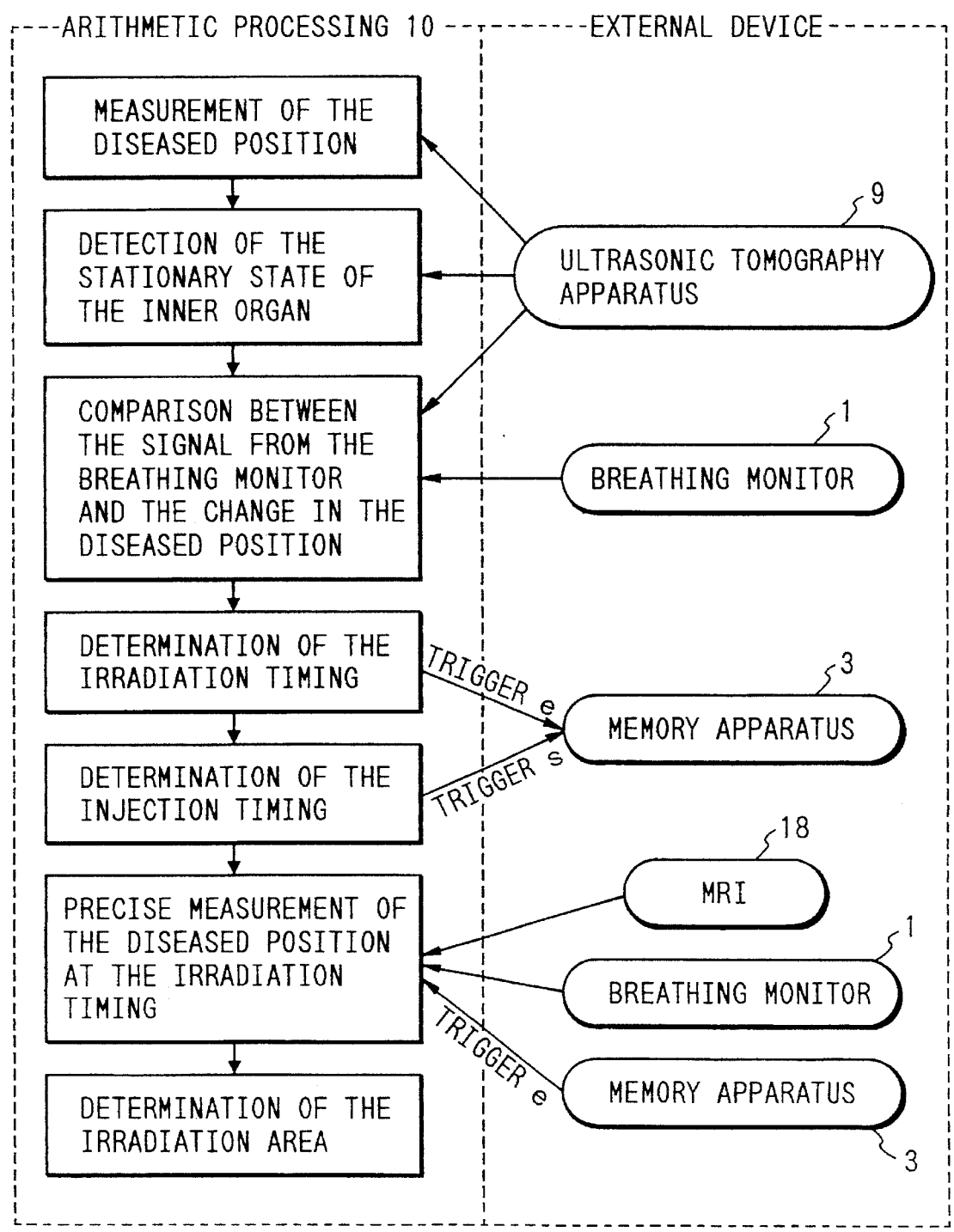
FIG. 10 is a flowchart showing the procedure for determining a correlation between the breathing of a patient and the position change of a diseased part of the patient.

FIG. 9 is a block diagram of a system for measuring concurrently the position of a diseased part of a patient and the time change of the breathing of the patient. FIG. 10 is a flow chart showing the operations in this system, which represents the input and output between the arithmetic processing apparatus 10 and its peripheral apparatus. In FIG. 9, the component 9a is a ultrasonic tomography apparatus, which gives a tomographic image of the area neighboring the diseased part from the ultrasonic signal detected by the probe 9b. The internal organs move periodically in synchronization with the breathing of the patient, and the timing when this movement becomes small, that is, a static period, can be recognized. Next, a signal which is synchronized with the breathing of the patient is detected and compared with the time change of the position of the diseased part. The component 1d is a sensor for measuring directly the flow rate of the breathing-in and the breathing-out, and its output signal is supplied to the breathing monitor 1c. Regarding methods for obtaining a signal changing in synchronization with the breathing of a patient, there are a method of measuring the temperature difference between the breathing-in flow and the breathing-out flow with a temperature sensor and a method of measuring the change in the chest measurement of the patient using a band wound around the chest of the patient, in addition to a method of measuring directly the flow rate of the breathing-in and the breathing-out of the patient. In addition, what can be adopted are a method for performing electromyography by measuring the electric signal corresponding to the expansion of the muscle with electrodes, and a method for measuring the output signal from an acceleration sensor mounted on the chest or the abdomen of the patient.

Suppose that the time change of the position of the diseased part (A) and the signal (B) from the breathing monitor are obtained as shown in the graph FIG. 11. The static period is the time when the curve A becomes lower, that is, the signal from the breathing monitor takes its local minimum value. The timing for initiating the radiation irradiation is selected to be the time when the signal from the breathing monitor takes its local minimum value, and this timing is stored in the memory means 3 as a timing for initiating the trigger e. Next, the timing for initiating the beam injection is set to be the timing when the signal from the breathing monitor takes its local maximum value, and is made to be stored in the memory means 3 as a timing for initiating the trigger s. Next, at the timing of trigger e, the tomographic imaging using nuclear magnetic resonance method (designated "MRI") is taken and the position and the shape of the diseased part is precisely measured. In a similar manner to the conventional radiation therapy, the region of the radiation irradiation and the dose of the irradiation are determined based on the precise measured data of the position and the shape of the diseased part. The precise measurement of the position of the diseased part can be done by an X-ray photography apparatus, other than MRI. An X-ray CT can be used for the apparatus for measuring precisely the position of the diseased part in real-time. The procedures up to here correspond to the step 1 shown in FIG. 1.

Figure 19:
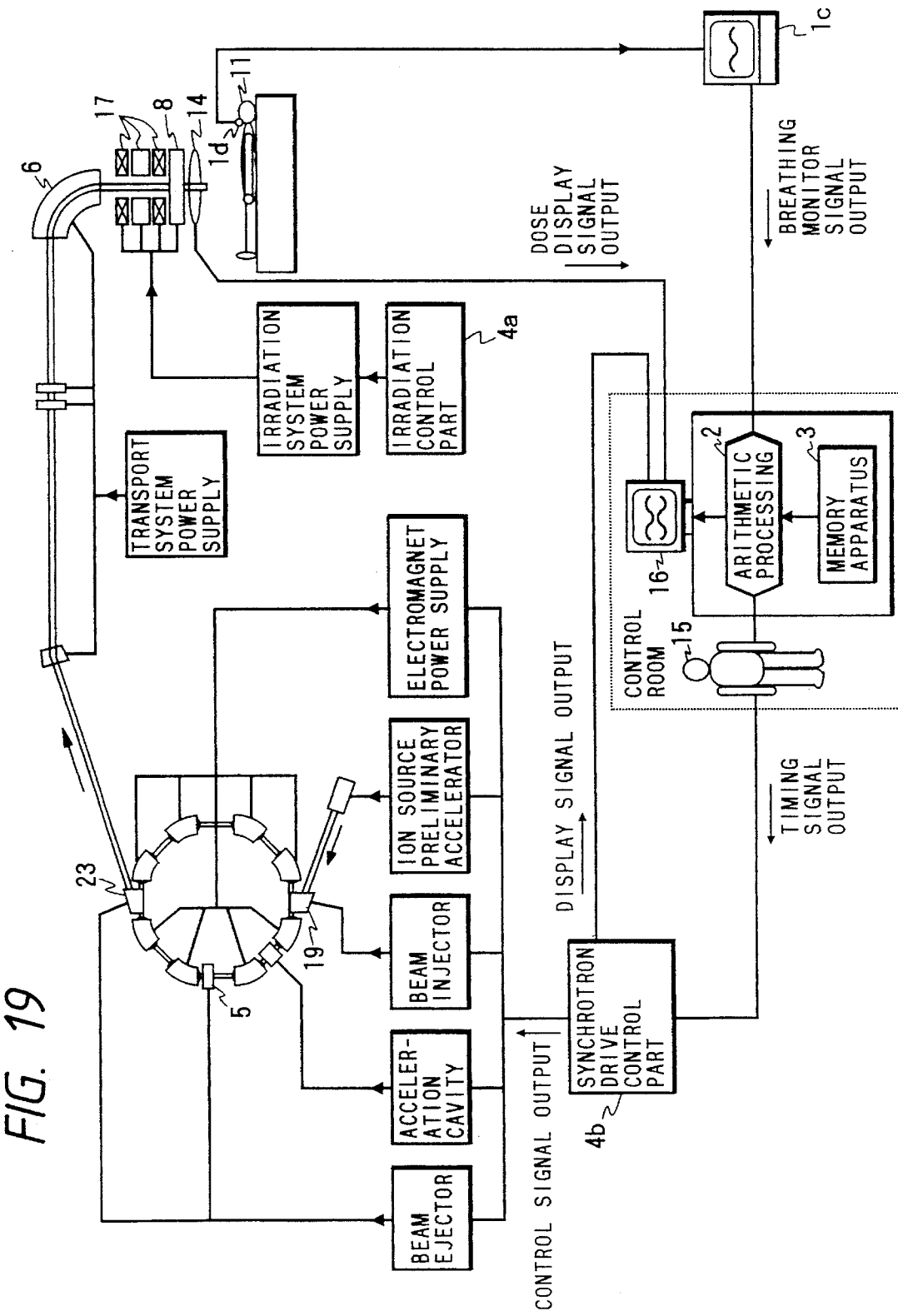
FIG. 19 is a diagrammatic configuration of a radiation therapy apparatus for controlling the ejection timing and the injection timing of a synchrotron using a fast ejection method in synchronization with the breathing of a patient.
Figure 20:
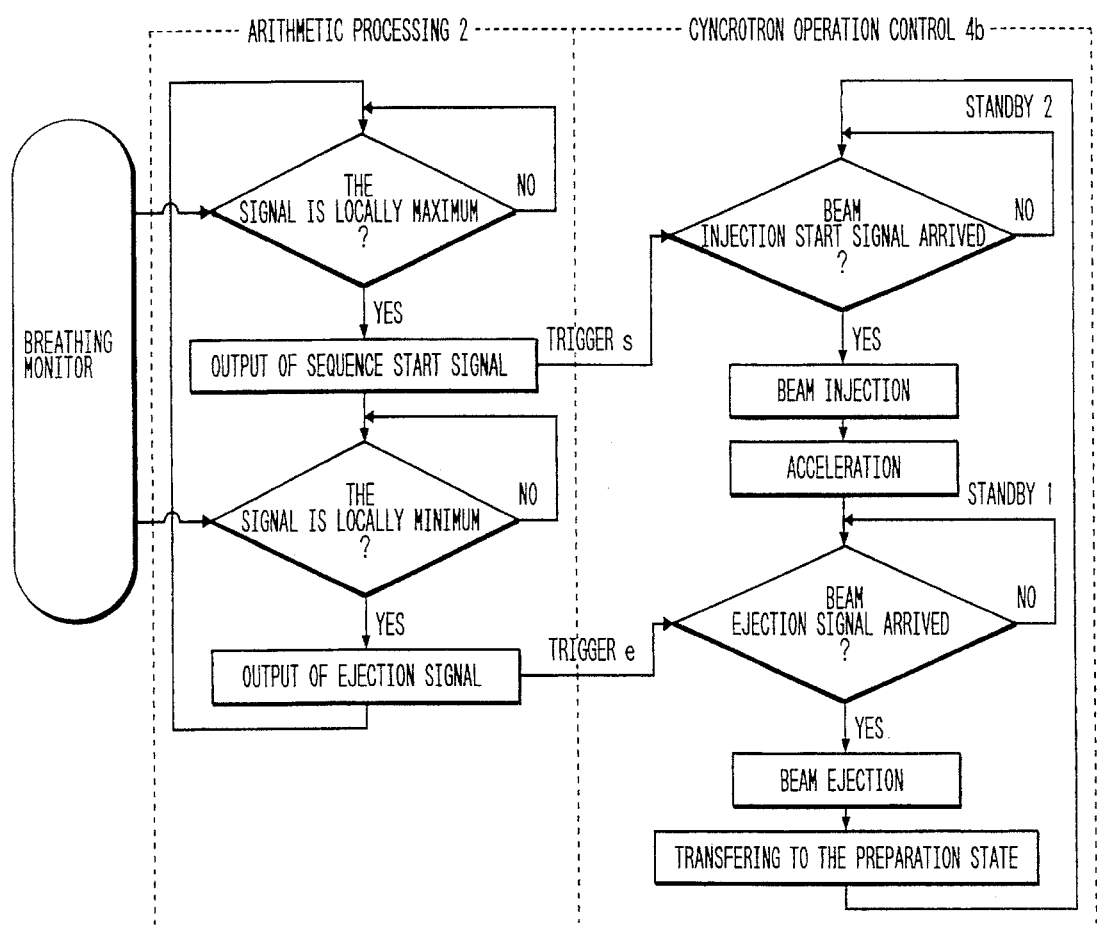
FIG. 20 is a flow chart showing the operation of a radiation therapy apparatus for controlling the ejection timing and the injection timing of a synchrotron using a fast ejection method in synchronization with the signal from a breathing monitor.
Figure 23:
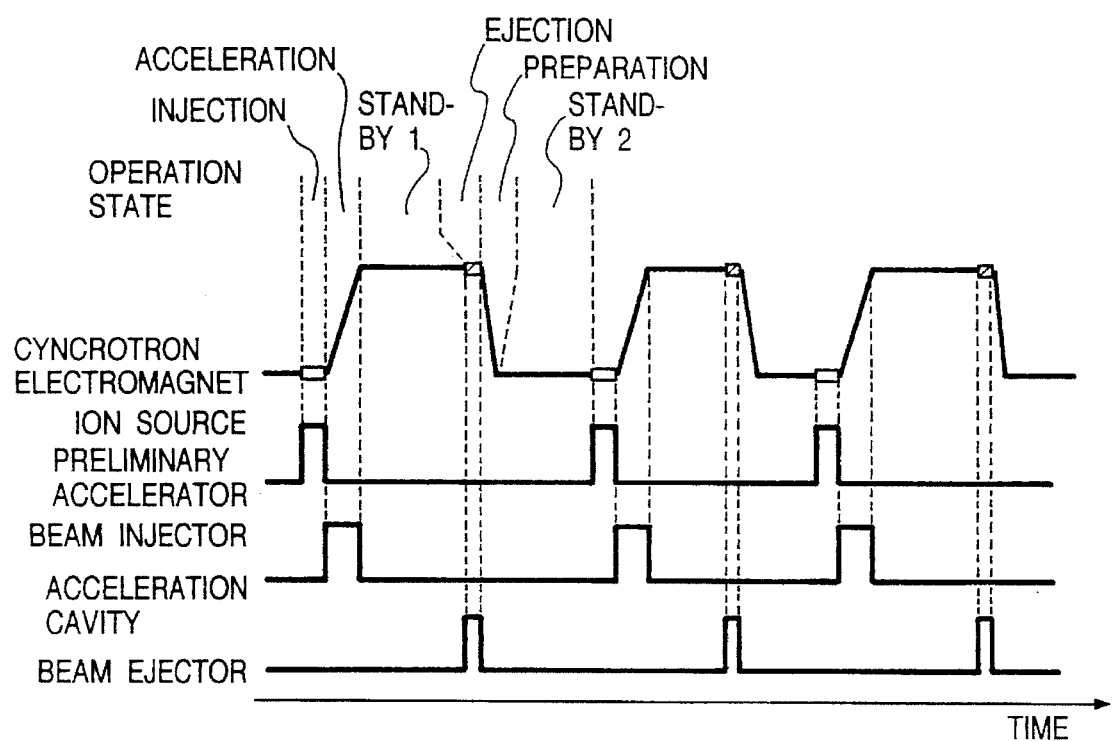
FIG. 23 is a timing chart showing the operation status of the individual parts of a synchrotron at each operation mode thereof.

Next, the procedure in the step 2 shown in FIG. 1 will be described. In FIG. 19, the component shaped in a circle is a synchrotron for accelerating charged particles, and its operation sequence is composed of injection, acceleration, standby 1, ejection, preparation and standby 2. The operation states of the individual parts of the apparatus at each operation mode are shown in FIG. 23. The operation of the transport system and the irradiation system is steady. The components 1c and 1d are the same breathing monitor and sensor as used in the step 1. The output signal from the breathing monitor is transferred to the arithmetic processing apparatus 2 in the control room. The arithmetic processing apparatus 2 has a different operation from that of the arithmetic processing apparatus 1. However, those two apparatus can be replaced by a single arithmetic processing apparatus including the integrated functions of those two apparatus. The curves B and C in FIG. 11 show the relationship between the output signal from the breathing monitor and the operation state of the accelerator. The procedure in the arithmetic processing apparatus 2 generating the trigger signals and the synchrotron operation control part 4b is shown in the flowchart in FIG. 20. When the signal from the breathing monitor takes its local maximum value, the arithmetic processing apparatus 2 supplies the trigger signal s to the synchrotron operation control part 4b in responsive to the timing stored in the memory apparatus 3. In response to the trigger signal s, the synchrotron operation control part injects the beam directed to the synchrotron by controlling the ion source, the preliminary accelerator and the injector. Next, in the synchrotron, the beam is accelerated by raising up the power supply level to the electromagnet by adjusting the voltage applied to the acceleration cavity and its frequency. After the acceleration, at the standby 1 mode, the control part 4b waits for the next trigger signal e. Next, when the signal from the breathing monitor takes its local minimum value, the arithmetic processing apparatus 2 supplies the trigger signal e to the synchrotron control part. The control part receives the trigger signal e, and shifts the trajectory of the beam by adjusting the kicker electromagnet 5 which is one of the ejectors, and thus, ejects the beam through the ejection deflector. The ejected beam is led through the transport system to the medical treatment room, and passes through the charged particle beam deflector 6, multiple-staged electromagnets for convergence and divergence for the beam line, and is finally exposed onto the diseased part. In case the acceleration is not terminated even when the trigger e has arrived, but the procedure has not yet reached the standby 1 state, the procedure does not move to the beam ejection, but waits for the termination of the acceleration. So far, the sequential steps from the start of the injection back to the standby 2 state of the acceleration, which is a single cycle of irradiation control, are repeated until the designated dose is irradiated. With this repetitive procedure, the dose of irradiation, synchronized to the signal from the breathing monitor, can be established. As the position and the shape of the diseased part do not change for the individual timing of irradiation, it is not required to shift the irradiation target area. Therefore, the parameter adjustment for the irradiation system and the transportation system is not necessary during the irradiation operation for therapy treatment. The signal from the breathing monitor, the signal showing the operation state of the synchrotron or the output signal from the charged particle beam current monitor 14 is displayed on the display device 16 in the control room, and thus, the operation for ejecting beams at a proper timing can be verified by the control operator 15. The accumulated dose of irradiation is measured by the charged particle beam current monitor 14, and the precise dose based on the therapy plan is irradiated.

Figure 13:
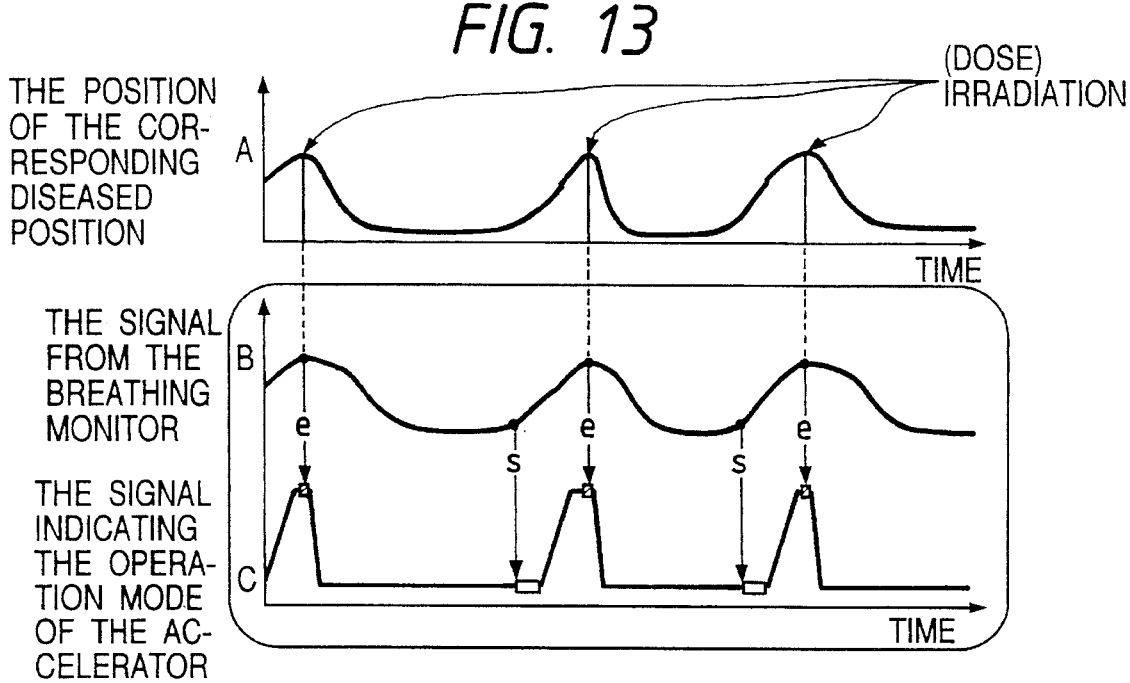
FIG. 13 is a timing chart showing the time change of the position of a diseased part (A), the output signal from a breathing monitor (B), and the operation state (C) of a synchrotron using a fast ejection method, in which an irradiation action is activated in a short period of time when the position of the diseased part reaches its peak.
Figure 14:
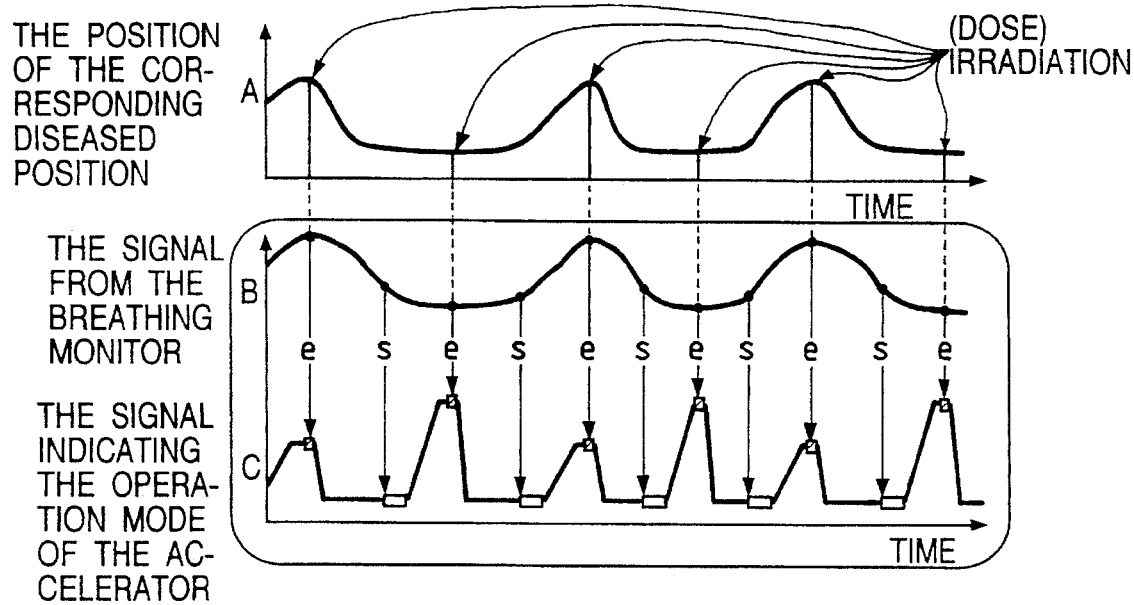
FIG. 14 is a timing chart showing the time change of the position of a diseased part (A), the output signal from a breathing monitor (B), and the operation state (C) of a synchrotron using a fast ejection method, in which two irradiation actions are activated during a single breathing action of the patient.

As for the setting of the timing of trigger signals, other than the method described above, it is possible to transfer immediately to the injection after the termination of the ejection, as shown in FIG. 12 where the trigger signal s is not used, and move to the standby state after the acceleration. It is also possible, as shown in FIG. 13, to eject the beam during a short period of time, when the output signal from the breathing monitor reaches its peak value and the position of the diseased part does not change, corresponding to the time from when the patient completes the breathing-in action until he/she starts the breathing-out action. In addition, as shown in FIG. 14, in case the operation sequence is repeated more rapidly, a plurality of beam ejections may be taken during a single breathing action by initiating a plurality of operation sequences at a plurality of timings in a single output signal from the breathing monitor. In this case, the irradiation target area is adjusted for the individual ejection, and thus, during a plurality of beam ejections for a single breathing action, the individual irradiation target areas are sequentially changed by controlling the irradiation system.

Next, there will be described an apparatus synchronizing its operation to the breathing of the patient, and in its own operation, in the radiation therapy operation performed thereby, when the position change of the diseased part is in synchronism with the breathing of the patient, after the charged particle beam is accelerated by a synchrotron, a relatively long pulse beam is ejected with an ejection method designated "slow ejection method" and is irradiated onto the diseased part. As the beam ejection using the slow ejection method can allow the straight part of the accelerator to be shorter than that in the fast ejection method, the size of the synchrotron can be made smaller than that of the previous embodiment.

As in the previous embodiment, the position of the diseased part and the time change of the breathing are measured concurrently. The procedure is similar to that in the previous embodiment except for the fact that the number of timings to be used is 1 greater. The arithmetic processing apparatus 10 defines how to determine the timing of the trigger signal to be supplied to the operation control part of the radiation irradiation apparatus. Suppose that the time change of the position of the diseased part and the signal from the breathing monitor are obtained as shown in the graphs A and B in FIG. 15. The timing for generating the first trigger signal s is set to be the time when the output signal from the breathing monitor takes its local maximum value. The timing for generating the second trigger signal e is set to be the time when the output signal from the breathing monitor decreases and its differentiation value goes closer to 0. The timing for generating the third trigger signal o is set to be the time when the output signal from the breathing monitor starts to rise up after this signal becomes lower. These methods for determining these timings, and corresponding functions, are stored in the memory apparatus. The procedure up to here corresponds to the step 1 in FIG. 1.

Figure 15:
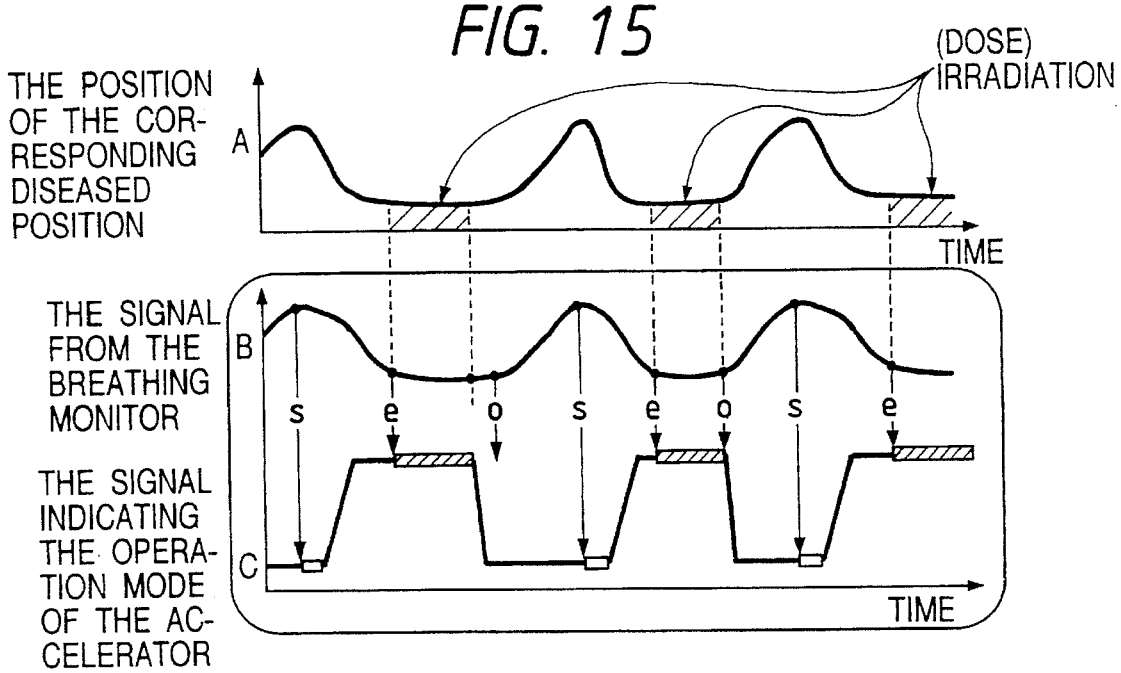
FIG. 15 is a timing chart showing the time change of the position of a diseased part (A), the output signal from a breathing monitor (B), and the operation state (C) of a synchrotron using a slow ejection method, in which a single irradiation action is activated by three trigger signals during a single breathing action of the patient.
Figure 22:
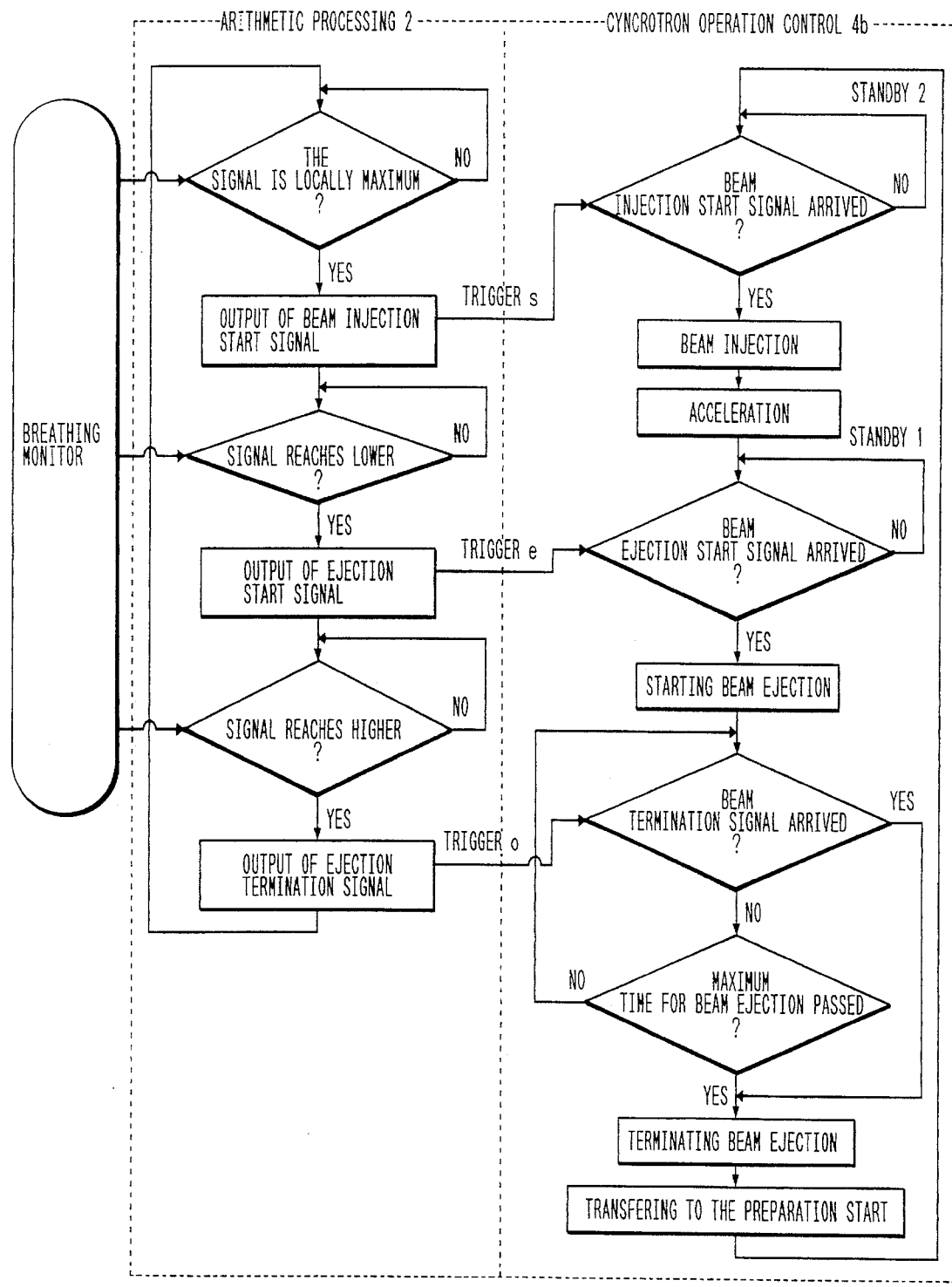
FIG. 22 is a flow chart showing the operation of a radiation therapy apparatus for controlling the ejection timing and the injection timing of a synchrotron using a slow ejection method in synchronization with the signal from a breathing monitor.

Next, the procedure corresponding to the step 2 in FIG. 1 will be described. The component shaped in a circle in FIG. 19 is a synchrotron for accelerating charged particles, and its operation sequence is composed of injection, acceleration, standby 1, ejection, preparation and standby 2. Unlike the previous embodiment, the ejection continues for about 0.5 second. The curves B and C in FIG. 15 show the relationship between the output signal from the breathing monitor and the operation state of the accelerator. The procedure in the arithmetic processing apparatus 2 generating the trigger signals and the synchrotron operation control part 4b is shown by the flowchart in FIG. 22. When the signal from the breathing monitor takes its local maximum value, the arithmetic processing apparatus 2 supplies the trigger signal s to the synchrotron operation control part 4b in response to the timing stored in the memory apparatus 3. In response to the trigger signal s, the synchrotron operation control part injects the beam directed to the synchrotron by controlling the ion source, the preliminary accelerator and the injector. Next, in the synchrotron, the beam is accelerated by raising up the power supply level to the electromagnet by adjusting the voltage applied to the acceleration cavity and its frequency. After acceleration, a bump trajectory is established. The bump trajectory is a trajectory with its partial shifted for ejection and formed by exciting the bump electromagnet 20.

By operating the quadrapole adjustment electromagnet 22 and the resonance excitation electromagnet 21, the unstable state of the beam is maintained so that the beam is easily ejected, and the arrival of the next trigger signal e is watched for at the standby 1 state. Next, when the trigger signal e is supplied from the arithmetic processing apparatus 2 to the synchrotron operation control part 4b, the beam is ejected and irradiated onto the target area of the diseased part by operating cooperatively the quadrapole adjustment electromagnet 22, the resonance excitation electromagnet 21, and the bump electromagnet 20. In case the acceleration is not completed even when the trigger signal e is issued, the ejection is started after the completion of the acceleration. Next, when the trigger signal o from the arithmetic processing apparatus 10 arrives at the synchrotron operation control part, in case the synchrotron is in the ejection state, the ejectors including the quadrapole adjustment electromagnet 22 are operated for terminating the ejection and the synchrotron moves into the preparation state before the next injection operation. In case the ejection is terminated before the arrival of the trigger signal o, the synchrotron moves into the preparation state independently without consideration of the arrival of the trigger signal o. Next, the synchrotron moves into the standby 2 state for waiting for the arrival of the trigger signal s for activating the next injection operation. So far, the sequential steps from the start of the injection back to the standby 2 state of the acceleration, which is a single cycle of irradiation control, are repeated until the designated dose is irradiated. With this repetitive procedure, a dose of irradiation, which is synchronized with to the signal from the breathing monitor, can be established. Since the position and the shape of the diseased part does not change for the individual timing of irradiation, it is not required to shift the irradiation target area. Therefore, the parameter adjustment for the irradiation system and the transportation system is not necessary during the irradiation operation for therapy treatment. The signal from the breathing monitor, the signal showing the operation state of the synchrotron or the output signal from the charged particle beam current monitor 14 is displayed on the display device 16 in the control room, and thus, the operation for ejecting beams at a proper timing can be verified by the control operator 1S. The accumulated dose of irradiation is measured by the charged particle beam current monitor 14, and the precise dose based on the therapy plan is irradiated. In case the current of the charged particle beam is so small that it is difficult to measure the current by the current monitor 14, an alternative way is possible in which the average ejection current per unit time is estimated with the average current during the synchrotron operation and the time necessary for the ejection, and the charged particle beam current is defined by multiplying the estimated average ejection current per unit time and the integrated value of the ejection time.

Figure 16:
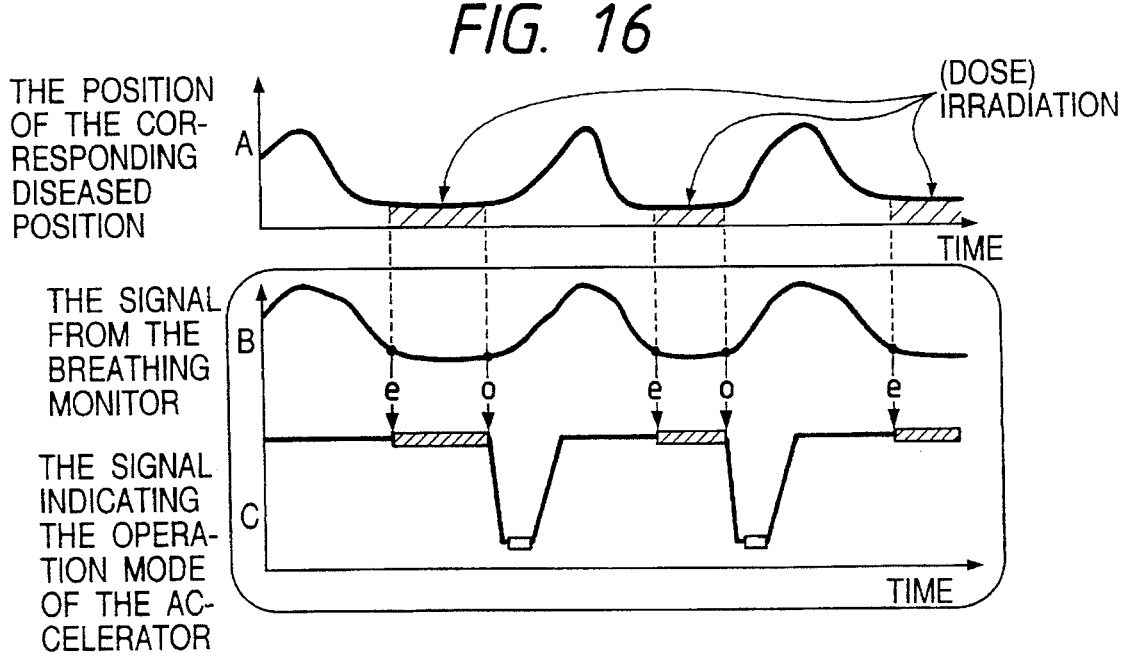
FIG. 16 is a timing chart showing the time change of the position of a diseased part (A), the output signal from a breathing monitor (B), and the operation state (C) of a synchrotron using a slow ejection method, in which a single irradiation action is activated by two trigger signals during a single breathing action of the patient.
Figure 17:
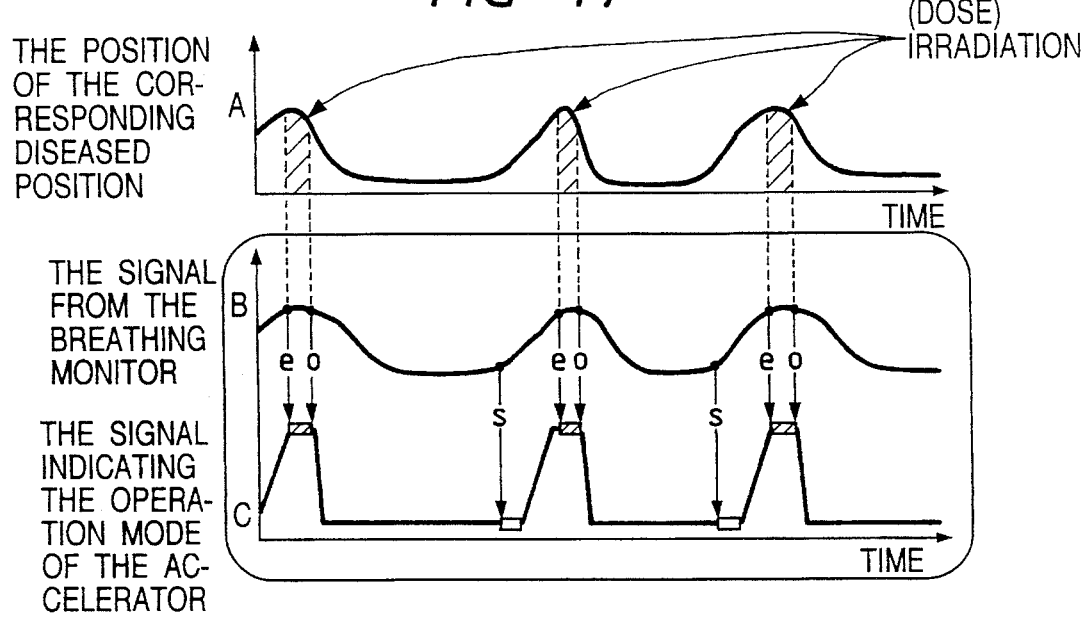
FIG. 17 is a timing chart showing the time change of the position of a diseased part (A), the output signal from a breathing monitor (B), and the operation state (C) of a synchrotron using a slow ejection method, in which an irradiation action is activated in a short period of time when the position of the diseased part reaches its peak.
Figure 18:
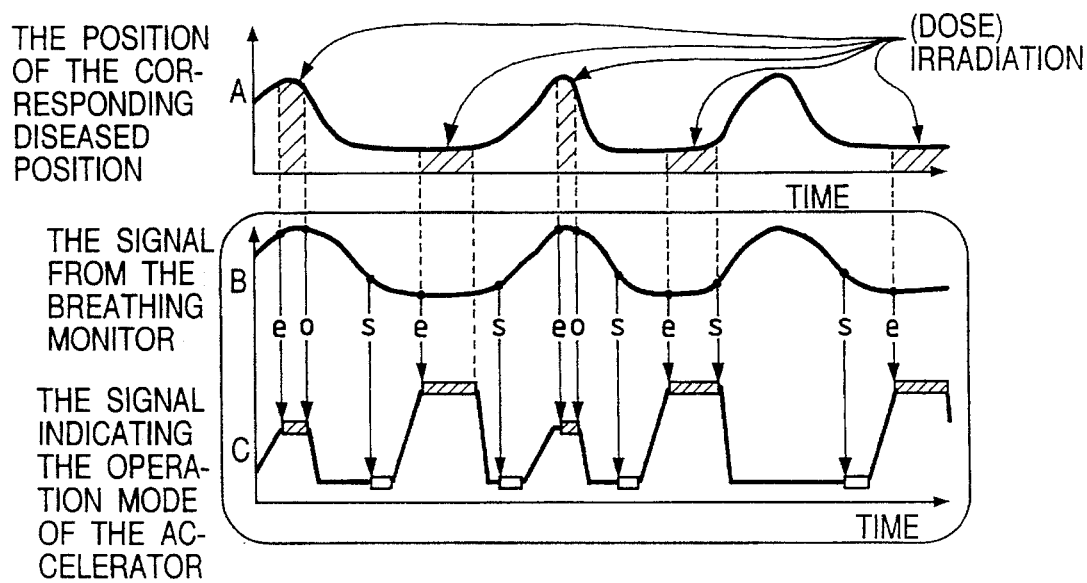
FIG. 18 is a timing chart showing the time change of the position of a diseased part (A), the output signal from a breathing monitor (B), and the operation state (C) of a synchrotron using a slow ejection method, in which two irradiation actions are activated during a single breathing action of the patient.

As for the setting of the timing of trigger signals, other than the method described above, it is permitted to transfer immediately to the injection state after the termination of the ejection, as shown in FIG. 16 where the trigger signal s is not used, and move to the standby state after the acceleration. It is also possible, as shown in FIG. 17, to eject the beam during a short period of time, when the output signal from the breathing monitor reaches its peak value and the position of the diseased part does not change corresponding to time, from the patient completes the breathing-in action until he/she starts the breathing-out action. In addition, as shown in FIG. 18, in case the operation sequence is repeated more rapidly, a plurality of beam ejections may be taken during a single breathing action by initiating a plurality of operation sequences at a plurality of timings in a single output signal from the breathing monitor. In this case, the irradiation target area is adjusted for the individual ejection, and thus, during a plurality of beam ejections for a single breathing action, the individual irradiation target areas are sequentially changed by controlling the irradiation system.

Next, there will be described an apparatus synchronizing its operation to the breathing of the patient, and its own operation, in the radiation therapy performed thereby, when the position change of the diseased part is in synchronism with the breathing of the patient, after the charged particle beam is accelerated by a synchrotron, a relatively long pulse beam is ejected with an ejection method designated "slow ejection method" and is irradiated onto the diseased part. As the beam ejection using the slow ejection method can allow the straight part of the accelerator to be shorter than that in the fast ejection method, the size of the synchrotron can be made smaller than that of the previous embodiment.

The step 1 of this embodiment is completely identical to the step 1 of the previous embodiment.

The procedures of the step 2 of this embodiment are almost the same as those of the step 2 of the previous embodiment.

Figure 21:
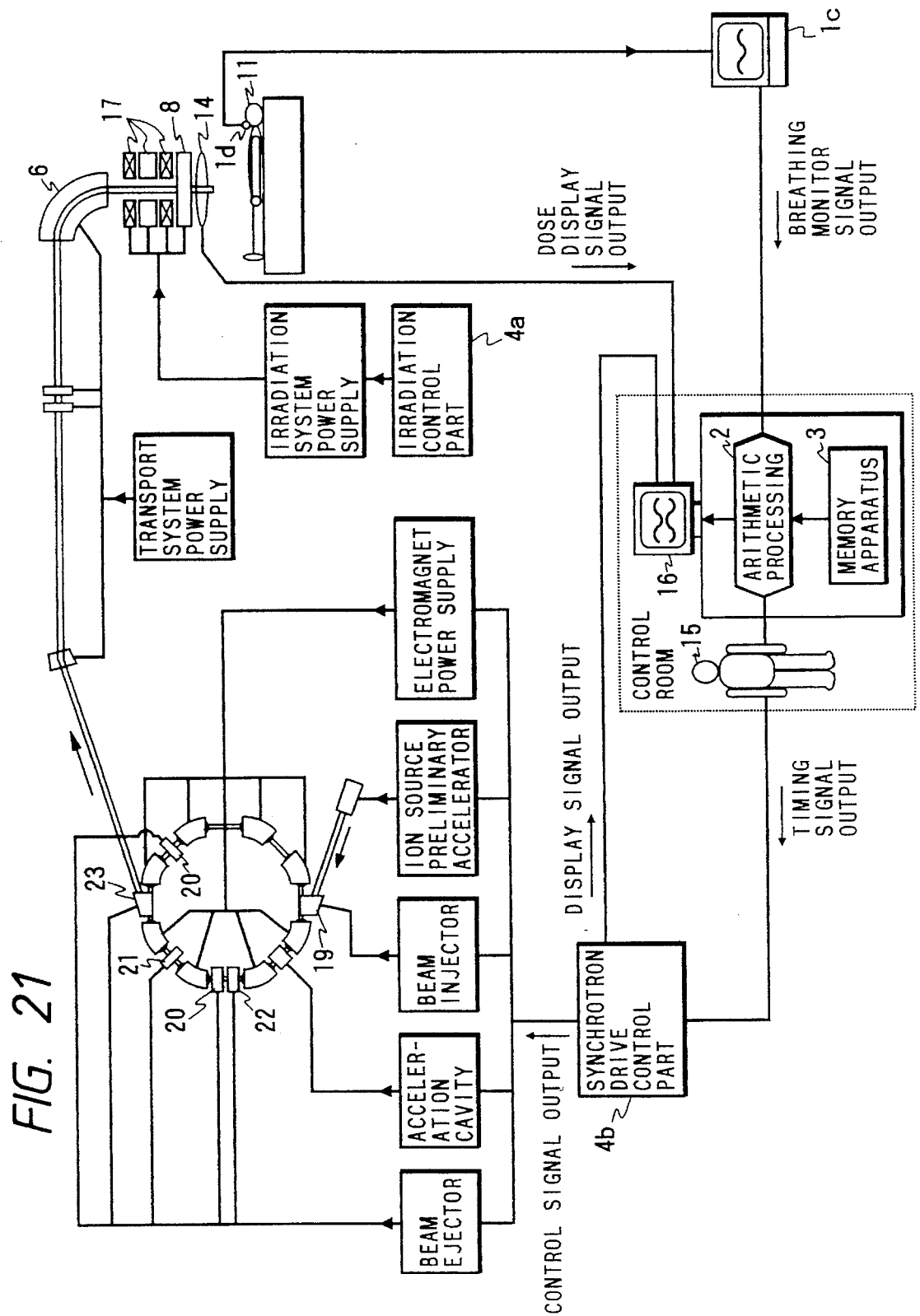
FIG. 21 is a diagrammatic configuration of a radiation therapy apparatus for controlling the ejection timing and the injection timing of a synchrotron using a slow ejection method in synchronization with the breathing of a patient.

The component shaped in a circle in FIG. 21 is a synchrotron for accelerating charged particles, and its operation sequence is composed of injection, acceleration, standby 1, ejection, preparation and standby 2. Similar to the previous embodiment, the ejection continues for about 0.5 second. The difference from the previous embodiment relates to the ejection method of the charged particle beam. In response to the trigger signal s, the synchrotron operation control part 4b injects and accelerates the beam under the operation sequence. After acceleration, a bump trajectory is established. By operating the quadrapole adjustment electromagnet 22 and the resonance excitation electromagnet 21, the unstable state of the beam is maintained so that it is easily ejected, and the arrival of the next trigger signal e is watched for at the standby 1 state. Next, when the trigger signal e is supplied from the arithmetic processing apparatus 2 to the synchrotron operation control part 4b, the beam is ejected by operating the high-frequency wave generation electrodes (not shown in the figure; mounted on a partial sector of the synchrotron shaped in a circle) as one of the components of the ejector for generating a high-frequency wave.

In case the acceleration is not yet terminated when the trigger signal e is issued, the ejection is activated after the completion of the acceleration. Next, when the trigger signal o is forwarded from the arithmetic processing part to the synchrotron operation control part, in case the synchrotron is in the ejection state, the ejection is terminated by terminating the generation of the high-frequency wave for ejection before moving to the preparation phase for the next injection operation. In case the ejection is terminated before the arrival of the trigger signal o, the synchrotron moves to the preparation state independently without consideration of the arrival of the trigger signal o. Finally, the synchrotron moves into the standby 2 state for waiting for the arrival of the trigger signal s for activating the next injection operation.

The timing setting for the trigger signals and the measurement of the cumulative dose irradiation onto the diseased part are similar to those in the previous embodiment.

According to the present invention, even with the diseased part moving in response to physical activity, the irradiation beam can be applied with an apparatus of simplified configuration.

As shown in the foregoing embodiments, the signal from the breathing monitor. The signal showing the operation state of the synchrotron or the output signal from the charged particle beam current monitor may be displayed on the display device 16 in the control room, and thus, the operation for ejecting beams at a proper timing can be verified by the control operator, the improper irradiation onto normal tissue due to an operation error can be prevented, and the safety and the reliability of the system can be raised. As shown in FIG. 12, by reducing the number of trigger signals issued, the operation of the accelerator can be simplified. AS shown in FIG. 14, a plurality of ejections are employed in a single breathing action, and so the efficiency of the dose of irradiation can be raised.

Since the straight part of the beam line in the accelerator using a "slow ejection method" for beam ejection is shorter than of the accelerator using a "fast ejection method", as shown in the embodiment of FIG. 15, the size of the synchrotron can be reduced, which results in the realization of a small-sized charged particle radiation therapy apparatus. At the same time, by irradiating a pulsed radiation beam having a relatively long pulse width using a "slow ejection method" the irradiation area on the target can be varied as time goes by, which enables a spatial scanning of the irradiation beam. Thus, also in the case of scanning the radiation beam over the position of the diseased part extended spatially, the irradiation can be optimized.

And furthermore, as shown in FIG. 6, by using a beam ejection method with a high-frequency wave, the cooperative and concurrent operation of the quadrapole adjustment electromagnet and the bump electromagnet, which has been always necessary conventionally, is not necessary. Owing to this method, the irradiation beam can be switched promptly with a simplified and small-sized apparatus, which enables a quick response to the medical treatment even when a sudden change of the patient condition occurs and the physical activity of the patient, such as a breathing cycle, changes irregularly, and thus ultimately, the precise definition of the irradiation area can be established.

I claim:

1. A radiation irradiation method, comprising the steps of:

detecting a signal representing a physical activity of a patient having a diseased area to be irradiated with radiation, said physical activity being an activity which causes periodic movement of the diseased area, and controlling a timing of radiation irradiation of said diseased area so that said irradiation is synchronized with said detected signal.

2. The radiation irradiation method defined in claim 1, wherein:

a relation between a time change of said physical activity of the patient as indicated by said detected signal and a position change of the diseased area is obtained, and radiation is activated when said position change of the diseased position becomes a minimum.

3. A radiation irradiation apparatus, comprising:

a detector for measuring a time change of a physical activity of a patient having a diseased area to be irradiated with radiation, said physical activity being an activity which causes periodic movement of the diseased area;

an information processing apparatus, connected to a memory apparatus for storing a relation between a detected signal from said detector indicating a time change of physical activity of the patient and a position change of said diseased area, for determining a radiation irradiation timing based on said detected signal from said detector and information from said memory means; and radiation control means for controlling timing of irradiation of said diseased area in response to an output signal from said information processing apparatus.

4. A radiation irradiation apparatus, comprising:

a particle accelerator for accelerating a charged particle; and an irradiation apparatus for irradiating said accelerated charged particle from said particle accelerator on a specified area of a patient;

a display apparatus for displaying an operation state of said particle accelerator; and a display apparatus for displaying a time change of physical activity of said patient, said physical activity being an activity which causes periodic movement of said specified area which said charged particle is irradiated.

5. A particle beam irradiation apparatus, comprising:

a particle accelerator for repeating periodically an operation sequence for injection, acceleration and ejection of a particle;

an irradiation apparatus for irradiating said accelerated particle on a specified area of a patient; and means for initiating said operation sequence of said particle accelerator at a designated timing in response to the breathing of said patient.

6. The particle beam irradiation apparatus defined in claim 5, wherein:

a particle beam is irradiated on said specified area once every time said patient takes a breath.

7. The particle beam irradiation apparatus defined in claim 5, wherein:

said designated timing of breathing of the patient is synchronized with either or both of a start of beam ejection and a termination of beam ejection of said particle accelerator.

8. The particle beam irradiation apparatus defined in claim 6, wherein:

said charged particle is injected and accelerated from a time when the patient starts breathing-in to a time when the patient terminates breathing-out, and said charged particle is ejected from a time when the patient terminates breathing-out to a time when the patient next starts breathing-in.

9. The particle beam irradiation apparatus defined in claim 6, wherein:

said charged particle is injected and accelerated from a time when the patient starts breathing-out to a time when the patient next terminates breathing-in, and said charged particle is ejected from a time when the patient terminates breathing-in to a time when the patient next starts breathing-out.

* * * * *